United States Patent
Xu

(10) Patent No.: US 12,036,019 B2
(45) Date of Patent: *Jul. 16, 2024

(54) METHOD AND SYSTEM FOR NON-INVASIVE OPTICAL BLOOD GLUCOSE DETECTION UTILIZING SPECTRAL DATA ANALYSIS

(71) Applicant: St. Louis Medical Devices, Inc., Sunnyvale, CA (US)

(72) Inventor: Zhi Xu, St. Louis, MO (US)

(73) Assignee: St. Louis Medical Devices, Inc., Sunnyvale, CA (US)

(\*) Notice: Subject to any disclaimer, the term of this patent is extended or adjusted under 35 U.S.C. 154(b) by 331 days.

This patent is subject to a terminal disclaimer.

(21) Appl. No.: 17/227,131

(22) Filed: Apr. 9, 2021

(65) Prior Publication Data

US 2021/0228117 A1 Jul. 29, 2021

Related U.S. Application Data

(60) Continuation of application No. 15/878,268, filed on Jan. 23, 2018, now Pat. No. 10,973,442, which is a (Continued)

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/1455* (2013.01); *A61B 5/6826* (2013.01);
(Continued)

(58) Field of Classification Search
CPC . A61B 5/14532; A61B 5/1455; A61B 5/6826; A61B 5/6838; A61B 5/7225
See application file for complete search history.

(56) References Cited

U.S. PATENT DOCUMENTS 2,441,343 A 5/1948 Becker
3,621,268 A 11/1971 Friedrich et al.
(Continued)

FOREIGN PATENT DOCUMENTS

CN 1192665 9/1998
CN 2694097 Y 4/2005
(Continued)

OTHER PUBLICATIONS

The Official Letter dated Mar. 19, 2021 for the European Patent Application No. 08836010.2.
(Continued)

*Primary Examiner* — Daniel L Cerioni
(74) *Attorney, Agent, or Firm* — Haverstock & Owens, A Law Corporation

(57) ABSTRACT

Systems and methods are disclosed for non-invasively measuring blood glucose levels in a biological sample based on spectral data. This includes a light source to strike a target area of a sample, a light detector positioned to receive light from the light source and to generate an output signal, having a time dependent current, which is indicative of the power of light detected, a processor to receive the output signal from the light detector based on the received output signal, calculate the attenuance attributable to blood in a sample present in the target area with a ratio factor, eliminate effect of uncertainty caused by temperature dependent detector response of the light detector, and then determine a blood glucose level associated with a sample present in the target area based on the calculated attenuance with the processor.

6 Claims, 4 Drawing Sheets

Related U.S. Application Data continuation of application No. 15/464,253, filed on Mar. 20, 2017, now Pat. No. 9,877,670, which is a continuation of application No. 13/610,423, filed on Sep. 11, 2012, now Pat. No. 9,629,576, which is a division of application No. 12/425,535, filed on Apr. 17, 2009, now Pat. No. 8,340,738.

(60) Provisional application No. 61/089,152, filed on Aug. 15, 2008, provisional application No. 61/055,303, filed on May 22, 2008.

(51) Int. Cl.
*A61B 5/1455* (2006.01)
*G16Z 99/00* (2019.01)

(52) U.S. Cl.
CPC .......... *A61B 5/6838* (2013.01); *A61B 5/7225* (2013.01); *G16Z 99/00* (2019.02); *A61B 2562/0238* (2013.01); *A61B 2576/00* (2013.01)

(56) References Cited

U.S. PATENT DOCUMENTS

| | | | |
|---|---|---|---|
| 3,910,701 A | 10/1975 | Henderson et al. | |
| 3,963,327 A | 6/1976 | Poirier | |
| 3,954,560 A | 10/1976 | Henderson et al. | |
| 4,014,321 A | 3/1977 | March | |
| 4,632,559 A | 12/1986 | Brunsting | |
| 4,655,225 A | 4/1987 | Dahne et al. | |
| 4,781,195 A | 11/1988 | Martin | |
| 4,836,782 A | 6/1989 | Gonser | |
| 4,962,311 A | 10/1990 | Poisel et al. | |
| 4,997,769 A | 3/1991 | Lundsgaard et al. | |
| 5,009,230 A | 4/1991 | Hutchison | |
| 5,028,787 A | 7/1991 | Rosenthal et al. | |
| 5,077,476 A | 12/1991 | Rosenthal | |
| 5,086,229 A | 2/1992 | Rosenthal et al. | |
| 5,112,124 A | 5/1992 | Harjunmaa et al. | |
| 5,137,023 A | 8/1992 | Mendelson et al. | |
| 5,167,228 A | 12/1992 | Czeisler | |
| 5,183,042 A | 2/1993 | Harjunmaa et al. | |
| 5,222,496 A | 6/1993 | Clarke et al. | |
| 5,255,171 A | 10/1993 | Clark | |
| 5,282,473 A | 2/1994 | Braig et al. | |
| 5,361,758 A | 11/1994 | Hall et al. | |
| 5,423,983 A | 6/1995 | Chiang et al. | |
| 5,448,992 A | 9/1995 | Kupershmidt | |
| 5,501,648 A | 3/1996 | Grigoriev | |
| 5,515,847 A | 5/1996 | Braig et al. | |
| 5,522,388 A | 6/1996 | Ishikawa et al. | |
| 5,529,065 A | 6/1996 | Tsuchiya | |
| 5,535,743 A | 7/1996 | Backhaus et al. | |
| 5,553,613 A | 9/1996 | Parker | |
| 5,576,544 A | 11/1996 | Rosenthal | |
| 5,643,334 A | 1/1997 | Eckhouse et al. | |
| 5,615,672 A | 4/1997 | Braig et al. | |
| 5,615,673 A | 4/1997 | Berger et al. | |
| 5,666,956 A | 9/1997 | Buchert | |
| 5,671,301 A | 9/1997 | Kupershmidt | |
| 5,703,364 A | 12/1997 | Rosenthal | |
| 5,743,262 A | 4/1998 | Lepper, Jr. et al. | |
| 5,910,109 A | 6/1999 | Peters et al. | |
| 6,025,597 A | 2/2000 | Sterling et al. | |
| 6,043,492 A | 3/2000 | Lee et al. | |
| 6,064,898 A | 5/2000 | Aldrich | |
| 6,067,463 A | 5/2000 | Jeng et al. | |
| 6,097,975 A | 8/2000 | Petrovsky et al. | |
| 6,134,458 A | 10/2000 | Rosenthal | |
| 6,134,460 A | 10/2000 | Chance | |
| 6,151,517 A | 11/2000 | Honigs et al. | |
| 6,167,290 A | 12/2000 | Yang et al. | |
| 6,181,958 B1 | 1/2001 | Steuer et al. | |
| 6,205,354 B1 | 3/2001 | Gellermann et al. | |
| 6,208,788 B1 | 3/2001 | Nosov | |
| 6,304,767 B1 | 10/2001 | Soller et al. | |
| 6,312,393 B1 | 11/2001 | Abreu | |
| 6,337,564 B2 | 1/2002 | Manzini et al. | |
| 6,403,944 B1 | 6/2002 | MacKenzie et al. | |
| 6,412,548 B1 | 7/2002 | Berman et al. | |
| 6,424,848 B1 | 7/2002 | Berman et al. | |
| 6,424,849 B1 | 7/2002 | Berman et al. | |
| 6,424,851 B1 | 7/2002 | Berman et al. | |
| 6,430,424 B1 | 9/2002 | Berman et al. | |
| 6,445,938 B1 | 9/2002 | Berman et al. | |
| 6,522,903 B1 | 2/2003 | Berman et al. | |
| 6,574,490 B2 | 6/2003 | Abbink et al. | |
| 6,671,528 B2 | 12/2003 | Steuer et al. | |
| 6,684,099 B2 | 1/2004 | Ridder et al. | |
| 6,723,048 B2 | 4/2004 | Fuller | |
| 6,731,963 B2 | 5/2004 | Finarov et al. | |
| 6,775,564 B1 | 8/2004 | Peters et al. | |
| 6,804,002 B2 | 10/2004 | Fine et al. | |
| 6,833,540 B2 | 12/2004 | MacKenzie et al. | |
| 6,865,408 B1 | 3/2005 | Abbink et al. | |
| 6,873,865 B2 | 3/2005 | Steuer et al. | |
| 6,958,039 B2 | 11/2005 | Burd et al. | |
| 6,968,222 B2 | 11/2005 | Burd et al. | |
| 6,990,365 B1 | 1/2006 | Parker et al. | |
| 6,993,372 B2 | 1/2006 | Fine et al. | |
| 7,039,446 B2 | 5/2006 | Ruchti et al. | |
| 7,039,447 B2 | 5/2006 | Berman et al. | |
| 7,043,289 B2 | 5/2006 | Fine et al. | |
| 7,107,087 B2 | 9/2006 | Hwang et al. | |
| 7,133,711 B2 | 11/2006 | Chemoguz et al. | |
| 7,215,987 B1 | 5/2007 | Sterling | |
| 7,254,432 B2 | 8/2007 | Fine et al. | |
| 7,266,400 B2 | 9/2007 | Fine et al. | |
| 7,409,239 B2 | 8/2008 | Chung et al. | |
| 7,424,317 B2 | 9/2008 | Parker et al. | |
| 7,436,511 B2 | 10/2008 | Ruchti et al. | |
| 7,509,153 B2 | 3/2009 | Blank | |
| 7,809,418 B2 | 10/2010 | Xu | |
| 7,961,305 B2 | 6/2011 | Xu et al. | |
| 8,272,771 B2 | 9/2012 | Arai | |
| 8,340,738 B2 | 12/2012 | Xu | |
| 2001/0030742 A1 | 10/2001 | Kramer et al. | |
| 2001/0039376 A1 | 11/2001 | Steuer et al. | |
| 2001/0047137 A1 | 11/2001 | Moreno et al. | |
| 2002/0010563 A1 | 1/2002 | Ratteree et al. | |
| 2002/0016534 A1 | 2/2002 | Trepagnier et al. | |
| 2002/0019055 A1 | 2/2002 | Brown et al. | |
| 2002/0038080 A1 | 3/2002 | Makarewicz et al. | |
| 2002/0091324 A1 | 7/2002 | Kollias et al. | |
| 2002/0161289 A1 | 10/2002 | Hopkins et al. | |
| 2002/0167704 A1 | 11/2002 | Kleinhans et al. | |
| 2003/0004423 A1 | 1/2003 | Lavie et al. | |
| 2003/0023140 A1 | 1/2003 | Chance | |
| 2003/0023152 A1 | 1/2003 | Abbink et al. | |
| 2003/0055325 A1 | 3/2003 | Weber et al. | |
| 2003/0078504 A1 | 4/2003 | Rowe | |
| 2003/0099574 A1 | 5/2003 | Bentsen | |
| 2004/0015734 A1 | 1/2004 | Rahman | |
| 2004/0087844 A1 | 5/2004 | Yen | |
| 2004/0106163 A1 | 6/2004 | Workman et al. | |
| 2004/0127779 A1 | 7/2004 | Steuer et al. | |
| 2004/0181132 A1 | 9/2004 | Rosenthal | |
| 2004/0204865 A1 | 10/2004 | Lee et al. | |
| 2004/0225205 A1 | 11/2004 | Fine et al. | |
| 2004/0225206 A1 | 11/2004 | Kouchnir | |
| 2005/0131286 A1 | 6/2005 | Parker et al. | |
| 2005/0197790 A1 | 9/2005 | Sterling et al. | |
| 2005/0256384 A1 | 11/2005 | Walker | |
| 2005/0261560 A1 | 11/2005 | Ridder et al. | |
| 2005/0272987 A1 | 12/2005 | Kian-Azarbayjany et al. | |
| 2005/0276072 A1 | 12/2005 | Hayashi et al. | |
| 2006/0002598 A1 | 1/2006 | Rowe et al. | |
| 2006/0004268 A1 | 1/2006 | Cho et al. | |
| 2006/0009685 A1 | 1/2006 | Finarov et al. | |
| 2006/0058622 A1 | 3/2006 | Tearney et al. | |
| 2006/0063983 A1 | 3/2006 | Yamakoshi | |
| 2006/0092643 A1 | 5/2006 | Wong et al. | |
| 2006/0129040 A1 | 6/2006 | Fine et al. | |
| 2006/0152726 A1 | 7/2006 | Larsen et al. | |

(56) References Cited

U.S. PATENT DOCUMENTS

| | | |
|---|---|---|
| 2006/0200014 A1 | 9/2006 | Fine et al. |
| 2006/0224057 A1 | 10/2006 | Burd et al. |
| 2006/0226992 A1 | 10/2006 | Al-Ali et al. |
| 2006/0234386 A1 | 10/2006 | Burns et al. |
| 2006/0250676 A1 | 11/2006 | Hagood |
| 2006/0258918 A1 | 11/2006 | Burd et al. |
| 2006/0264719 A1 | 11/2006 | Schurman et al. |
| 2007/0049811 A1 | 3/2007 | Kobayashi et al. |
| 2007/0078312 A1 | 4/2007 | Fine et al. |
| 2007/0112258 A1 | 5/2007 | Soyemi et al. |
| 2007/0149869 A1 | 6/2007 | Yen |
| 2007/0179367 A1 | 8/2007 | Ruchti |
| 2008/0027297 A1 | 1/2008 | Yamakoshi |
| 2008/0137066 A1 | 6/2008 | Weinstein |
| 2008/0144004 A1 | 6/2008 | Rosenthal |
| 2008/0194014 A1 | 8/2008 | Young et al. |
| 2008/0266900 A1 | 10/2008 | Harbers et al. |
| 2008/0316488 A1 | 12/2008 | Mao |
| 2009/0059586 A1 | 3/2009 | Livesay et al. |
| 2009/0079964 A1 | 3/2009 | Xu |
| 2009/0105565 A1 | 4/2009 | Xu |
| 2009/0105605 A1 | 4/2009 | Abreu |
| 2009/0116017 A1 | 5/2009 | Xu et al. |
| 2009/0196025 A1 | 8/2009 | Joseph et al. |
| 2009/0247843 A1 | 10/2009 | Xu |
| 2009/0270700 A1 | 10/2009 | Van Herpen et al. |
| 2009/0292186 A1 | 11/2009 | Xu |
| 2010/0026995 A1 | 2/2010 | Merrit et al. |
| 2010/0252721 A1 | 10/2010 | Xu |
| 2013/0006070 A1 | 1/2013 | Xu |
| 2013/0006072 A1 | 1/2013 | Ku |
| 2013/0006073 A1 | 1/2013 | Ku |

FOREIGN PATENT DOCUMENTS

| | | | |
|---|---|---|---|
| CN | 1932840 A | | 3/2007 |
| EP | 0160768 A1 | | 11/1985 |
| EP | 0319159 A1 | | 6/1989 |
| EP | 0781527 A1 | | 7/1997 |
| EP | 01094745 A1 | | 5/2001 |
| EP | 1281370 A2 | | 2/2003 |
| EP | 1300712 A2 | | 4/2003 |
| EP | 830582 B1 | | 8/2005 |
| GB | 810256 A | | 3/1959 |
| JP | 56-156138 A | | 12/1981 |
| JP | 02-191434 A | | 7/1990 |
| JP | 07-088105 A | | 4/1995 |
| JP | 720551 U | | 4/1995 |
| JP | 9010238 | | 1/1997 |
| JP | H0956702 A | | 3/1997 |
| JP | 11037931 A | | 2/1999 |
| JP | 11-178813 A | | 7/1999 |
| JP | 2000083933 A | | 3/2000 |
| JP | 2003245265 A | | 9/2003 |
| JP | 2004267613 A | | 9/2004 |
| JP | 2004286475 A | | 10/2004 |
| JP | 2004290544 A | | 10/2004 |
| JP | 2004538054 A | | 12/2004 |
| JP | 2005283563 A | | 10/2005 |
| JP | 2007185348 A | | 7/2007 |
| JP | 2009545344 A | | 12/2009 |
| RU | 2050545 C1 | | 12/1995 |
| RU | 2188425 C2 | | 8/2002 |
| RU | 2198402 C2 | | 2/2003 |
| SU | 1193541 A1 | | 11/1985 |
| WO | 90/130922 A1 | | 11/1990 |
| WO | 1991015991 A1 | | 10/1991 |
| WO | 1991015992 A1 | | 10/1991 |
| WO | 92/00513 A1 | | 1/1992 |
| WO | 1993000856 A1 | | 1/1993 |
| WO | 93/06774 A1 | | 4/1993 |
| WO | 93/16629 A1 | | 9/1993 |
| WO | 1994013199 A1 | | 6/1994 |
| WO | 1994016614 A1 | | 8/1994 |
| WO | 95/05599 A1 | | 2/1995 |
| WO | 1995031930 A1 | | 11/1995 |
| WO | 1996004840 A1 | | 2/1996 |
| WO | 1996017546 A1 | | 6/1996 |
| WO | 96/39926 A1 | | 12/1996 |
| WO | 96/41151 A1 | | 12/1996 |
| WO | 1996039927 A1 | | 12/1996 |
| WO | 1998003847 A2 | | 1/1998 |
| WO | 1998036681 A1 | | 8/1998 |
| WO | 99/16136 A1 | | 4/1999 |
| WO | 199939631 A1 | | 8/1999 |
| WO | 2000001294 A1 | | 1/2000 |
| WO | 2000016688 A1 | | 3/2000 |
| WO | 01/16578 A1 | | 3/2001 |
| WO | 2001093755 A1 | | 12/2001 |
| WO | 2001096872 A2 | | 12/2001 |
| WO | 2002082990 A1 | | 10/2002 |
| WO | 03001177 A2 | | 1/2003 |
| WO | 2003010510 A2 | | 2/2003 |
| WO | 03/077756 A1 | | 9/2003 |
| WO | 2003079900 A1 | | 10/2003 |
| WO | 2005045377 A2 | | 5/2005 |
| WO | 2006086566 A2 | | 8/2006 |
| WO | 2006094109 A1 | | 9/2006 |
| WO | 2007122557 A2 | | 11/2007 |
| WO | 2008014890 A1 | | 2/2008 |
| WO | 2008/039195 A1 | | 4/2008 |
| WO | 2009/035669 A1 | | 3/2009 |
| WO | 2009/045492 A1 | | 4/2009 |
| WO | 2009/120600 A2 | | 10/2009 |
| WO | 2009/142853 A1 | | 11/2009 |
| WO | 2010017238 A1 | | 2/2010 |
| WO | 2010114736 | | 10/2010 |

OTHER PUBLICATIONS

Wagner et al., "Invasiveness as a Barrier to Self-Monitoring of Blood Glucose in Diabetes", Diabetes Technology & Therapeutics, Aug. 1, 2005.
Web Page Document entitled http://www.orense.com/Diabetes_Monitoring dated Aug. 9, 2007.
International Search Report for PCT/US/2008/010670 dated Nov. 21, 2008.
International Search Report for PCT/US/2008/011438 dated Dec. 9, 2008.
Office Action for U.S. Appl. No. 12/209,807 dated May 17, 2010.
International Search Report and Written Opinion for PCT/US2010/028255 dated May 19, 2010.
Office Action for U.S. Appl. No. 12/256,028 dated May 24, 2010.
International Preliminary Report on Patentability (Chapter II) for PCT/US2008/011438 dated Jun. 18, 2010.
Office Action for U.S. Appl. No. 12/256,028 dated Sep. 15, 2010.
Office Action for U.S. Appl. No. 12/209,807 dated Sep. 17, 2010.
International Preliminary Report on Patentability (Chapter II) for PCT/US2009/040942 dated Dec. 13, 2010.
Office Action for U.S. Appl. No. 12/425,535 dated Mar. 22, 2012.
Office Action for U.S. Appl. No. 12/407,999 dated Apr. 6, 2012.
Office Action for U.S. Appl. No. 12/425,535 dated May 16, 2012.
Office Action for CN Application 200980126116.7 dated Jun. 4, 2012.
Office Action for RU Application 2010117396 dated Jun. 18, 2012.
Office Action for RU Application 2010114587 dated Jun. 22, 2012.
Office Action for U.S. Appl. No. 12/729,886 dated Oct. 2, 2012.
Office Action for U.S. Appl. No. 12/407,999 dated Nov. 21, 2012.
Office Action for JP Application 2010-524873 dated Dec. 25, 2012.
Office Action for JP Application 2010-527994 dated Dec. 25, 2012.
Office Action for CN Application 200880114960.3 dated Jan. 29, 2013.
Office Action for CN Application 200980126116.7 dated Feb. 16, 2013.
Office Action for U.S. Appl. No. 12/729,886 dated Mar. 12, 2013.
Office Action for RU Application 2010152373 dated Mar. 26, 2013.
Extended European Search Report for EP Application 08830786.3 dated Apr. 22, 2013.

(56) References Cited

OTHER PUBLICATIONS

Office Action for JP Application 2011-501936 dated Jun. 25, 2013.
Office Action for CN Application 201080022242.0 dated Jul. 4, 2013.
Extended European Search Report for EP Application 09751083.8 dated Jul. 26, 2013.
Office Action for AU Application 2010232841 dated Aug. 13, 2013.
Office Action for AU Application 2008299938 dated Sep. 13, 2013.
Office Action for U.S. Appl. No. 12/407,999 dated Oct. 10, 2013.
Office Action for CN Application 200980126116.7 dated Oct. 17, 2013.
Office Action for JP Application 2010-524873 dated Nov. 19, 2013.
Office Action for JP Application 2011-510533 dated Dec. 3, 2013.
Examiner's Decision of Rejection for JP Application 2010-527994 dated Dec. 10, 2013.
Office Action for CN Application 201210419849.3 dated Jan. 6, 2014.
Office Action for EP Application 08830786.3 dated Jan. 10, 2014.
Office Action for CN Application 201210420843.8 dated Feb. 17, 2014.
Office Action for CN Application 201210419740.X dated Feb. 28, 2014.
Office Action for CN Application 201080022242.0 dated Mar. 12, 2014.
Office Action for RU Application 2010114587 dated Mar. 25, 2014.
Office Action for EP Application 09751083.8 dated Mar. 28, 2014.
Office Action for CA Application 2700996 dated Jul. 30, 2014.
Office Action for JP Application 2011-501936 dated Aug. 5, 2014.
Office Action for U.S. Appl. No. 12/407,999 dated Nov. 20, 2014.
Office Action for CN Application 201210420830.0 dated Jan. 5, 2015.
Office Action for U.S. Appl. No. 13/610,342 dated Jan. 21, 2015.
Office Action for U.S. Appl. No. 13/610,423 dated Jan. 22, 2015.
Office Action for U.S. Appl. No. 13/610,387 dated Jan. 22, 2015.
Brazilian Office Action dated Mar. 10, 2022, Application No. PI0818177-2.
Office Action for CN Application 200880114960.3 dated Feb. 17, 2015.
Office Action for EP Application 09751083.8 dated Feb. 24, 2015.
Office Action for CN Application 201310489245.0 dated Feb. 26, 2015.
Office Action for CA Application 2699626 dated Feb. 27, 2015.
Office Action for JP Application 2012-503498 dated Mar. 31, 2015.
Office Action dated for RU Application 2011144084 dated Apr. 17, 2015.
Office Action for CA Application 2700996 dated Aug. 7, 2015.
Office Action for U.S. Appl. No. 12/407,999 dated Jan. 5, 2016.
Office Action for JP Application 2014-245584 dated Jan. 5, 2016, includes English Translation.
Office Action for CN Application 201310489245 dated Jan. 25, 2016.
Office Action for EP Application 9751083.8 dated Jan. 26, 2016.
Extended European Search Report for EP Application 08836010.2 dated Mar. 8, 2016.
Office Action for U.S. Appl. No. 13/610,423 dated Mar. 24, 2016.
Office Action for CA Application 2789658 dated Mar. 30, 2016.
Office Action for U.S. Appl. No. 13/610,342 dated Apr. 14, 2016.
Office Action for U.S. Appl. No. 13/610,387 dated Apr. 14, 2016.
Office Action for U.S. Appl. No. 13/610,140 dated May 13, 2016.
International Preliminary Report on Patentability (Chapter II) for PCT/US2009/037805 dated Dec. 14, 2010.
First Examination Report dated Oct. 27, 2017 for the Indian Application No. 1186/KOLNP/2010.
European Search Report from European Application No. 17159427.8.
Attached please find the Office Action dated Jun. 30, 2017 for the Indian application No. 4886/KOLNP/2010.
Texas Instruments TSL260, TSL261, TSL262 IR Light-to-Voltage Optical Sensors 1993.
Indian Examination Report dated Apr. 13, 2018, Application No. 41144/KOLNP/2011.
European First Examination Report dated Jun. 4, 2018. EP Application No. 10759220.6.
Unfavorable opinion dated Jul. 31, 2019 for Brazilian Application No. PI01816925-0.
European Search Report dated Aug. 21, 2019 for European Application No. 19178081.6.
The Office Action dated Dec. 21, 2018 for Brazilian Patent Application No. PI0816925-0.
The Office Action dated May 21, 2019 for Brazilian Patent Application No. PI0909825-9.
The Office Action dated Jul. 7, 2020 for the Brazilian application No. PI1010304-0.
The Hearing Notice dated Nov. 8, 2019 form Indian Patent application No. 1186/KOLNP/2010.
he Decision for Refusal dated Feb. 13, 2020, from European Patent Application No. EP 10 759 220.6.

METHOD AND SYSTEM FOR NON-INVASIVE OPTICAL BLOOD GLUCOSE DETECTION UTILIZING SPECTRAL DATA ANALYSIS

CROSS-REFERENCE TO RELATED APPLICATION

This application is a continuation patent application of co-pending U.S. patent application Ser. No. 15/878,268, filed Jan. 23, 2018, and entitled METHOD AND SYSTEM FOR NON-INVASIVE OPTICAL BLOOD GLUCOSE DETECTION UTILIZING SPECTRAL DATA ANALYSIS, which is a continuation patent application of U.S. patent application Ser. No. 15/464,253, filed Mar. 20, 2017, and entitled METHOD AND SYSTEM FOR NON-INVASIVE OPTICAL BLOOD GLUCOSE DETECTION UTILIZING SPECTRAL DATA ANALYSIS, which is a continuation patent application of U.S. patent application Ser. No. 13/610,423, filed Sep. 11, 2012, issued as U.S. Pat. No. 9,629,576 and entitled METHOD AND SYSTEM FOR NON-INVASIVE OPTICAL BLOOD GLUCOSE DETECTION UTILIZING SPECTRAL DATA ANALYSIS, which is a divisional of prior U.S. Patent Application Number 12/425,535, filed Apr. 17, 2009, issued as U.S. Pat. No. 8,340,738, which are all hereby incorporated herein by reference in their entirety, and also claims priority to U.S. Provisional Patent Application Ser. No. 61/055,303, filed on May 22, 2008, the disclosure of which is incorporated herein by reference, and also claims priority to U.S. Provisional Patent Application Serial Number 61/089,152, filed on Aug. 15, 2008, the disclosure of which is incorporated herein by reference.

BACKGROUND OF THE INVENTION

Diabetes is a chronic disease that, when not controlled, over time leads to serious damage to many of the body's systems, including the nerves, blood vessels, eyes, kidneys and heart. The National institute of Diabetes and Digestive and Kidney Diseases (NIDDK) estimates that 23.6 million people, or 7.8 percent of the population in the United States, had diabetes in 2007. Globally, the World Health Organization (WHO) estimates that more than 180 million people have diabetes, a number they expect to increase to 366 million by 2030, with 30.3 million in the United States. According to the WHO, an estimated 1.1 million people died from diabetes in 2005. They project that diabetes deaths will increase by more than 50% between 2006 and 2015 overall and by more than 80% in upper-middle income countries.

The economic burden from diabetes for individuals and society as a whole is substantial. According to the American Diabetes Association, the total annual economic cost of diabetes was estimated to be $174 billion in the United States in 2007. This is an increase of $42 billion since 2002. This 32% increase means the dollar amount has risen over 58 billion more each year.

A vital element of diabetes management is the self-monitoring of blood glucose (SMBG) concentration by diabetics in the home environment. By testing blood glucose levels often, diabetics can better manage medication, diet, and exercise to maintain control and prevent the long-term negative health outcomes. In fact, the Diabetes Control and Complications Trial (DCCT), which followed 1,441 diabetics for several years, showed that those following an intensive-control program with multiple blood sugar tests each day, as compared with the standard-treatment group, had only one-fourth as many people develop diabetic eye disease, half as many develop kidney disease, one-third as many develop nerve disease, and far fewer people who already had early forms of these three complications got worse.

However, current monitoring techniques discourage regular use due to the inconvenient and painful nature of drawing blood through the skin prior to analysis, which causes many diabetics to not be as diligent as they should be for good blood glucose control. As a result, non-invasive measurement of glucose concentration is a desirable and beneficial development for the management of diabetes. A non-invasive monitor will make testing multiple times each day pain-free and more palatable for children with diabetes. According to a study published in 2005 (J. Wagner, C. Malchoff, and G. Abbott, Diabetes Technology & Therapeutics, 7(4) 2005, 612-619), people with diabetes would perform SMBG more frequently and have improved quality of life with a non-invasive blood glucose monitoring device.

There exist a number of non-invasive approaches for blood glucose determination. One technique of non-invasive blood chemical detection involves collecting and analyzing light spectra data.

Extracting information about blood characteristics, such as glucose concentration from spectral or other data obtained from spectroscopy, is a complex problem due to the presence of components (e.g., skin, fat, muscle, bone, interstitial fluid) other than blood in the area that is being sensed. Such other components can influence these signals in such a way as to alter the reading. In particular, the resulting signal may be much larger in magnitude than the portion of the signal that corresponds to blood, and therefore limits the ability to accurately extract blood characteristics information.

The present invention is directed to overcoming one or more of the problems set forth above.

SUMMARY OF INVENTION

In an aspect of the present invention, a method for detecting glucose in a biological sample is disclosed. The method includes utilizing at least one light source configured to strike a target area of a sample, utilizing at least one light detector positioned to receive light from the at least one light source and to generate an output signal, having a time dependent current, which is indicative of the power of light detected, receiving the output signal from the at least one light detector with a processor and based on the received output signal, calculating the attenuance attributable to blood in a sample present in the target area with a ratio factor with the processor, eliminating effect of uncertainty caused by temperature dependent detector response of the at least one light detector with the processor, and determining a blood glucose level associated with a sample present in the target area with the processor based on the calculated attenuance with the processor.

In yet another aspect of the present invention, a system for detecting glucose in a biological sample is disclosed. This system includes at least one light source configured to strike a target area of a sample, at least one light detector positioned to receive light from the at least one light source and to generate an output signal, having a time dependent current, which is indicative of the power of light detected, a processor configured to receive the output signal from the at least one light detector based on the received output signal, calculate the attenuance attributable to blood in a sample present in the target area with a ratio factor, eliminate effect of uncertainty caused by temperature dependent detector response of the at least one light detector, and then determine a blood glucose level associated with a sample present in the target area based on the calculated attenuance with the processor.

These are merely some of the innumerable aspects of the present invention and should not be deemed an all-inclusive listing of the innumerable aspects associated with the present invention.

BRIEF DESCRIPTION OF THE DRAWINGS

For a better understanding of the present invention, reference may be made to accompanying drawings, in which.

DETAILED DESCRIPTION OF THE INVENTION

In the following detailed description, numerous exemplary specific details are set firth in order to provide a thorough understanding of the invention. However, it will be understood by those skilled in the art that the present invention may be practiced without these specific details, or with various modifications of the details. In other instances, well known methods, procedures, and components have not been described in detail so as not to obscure the present invention.

Optical spectroscopy can be used to determine the amount of light absorbed and scattered, i.e., attenuated, by a biological sample such as a human finger. By measuring the amount of light absorbed by the sample, it is possible to determine glucose, cholesterol, and hemoglobin levels of a subject non-invasively. Fingertip measurements are usually preferred because of the large concentration of capillaries in the fingertip and because of the conversion of arterial blood into venous blood that occurs in the fingertip. However, the techniques of the present invention are not limited to use with a fingertip. For example, the biological sample could be a human earlobe.

When light is transmitted through a biological sample, such as a human finger, the light is attenuated by various components of the finger including skin, muscle, bone, fat, interstitial fluid and blood. It has been observed, however, that light attenuation by a human finger exhibits a small cyclic pattern that corresponds to a heartbeat. It is believed that this cyclic pattern will be present in measurements of many other human body parts, the earlobe being one of many examples.

Figure 1:
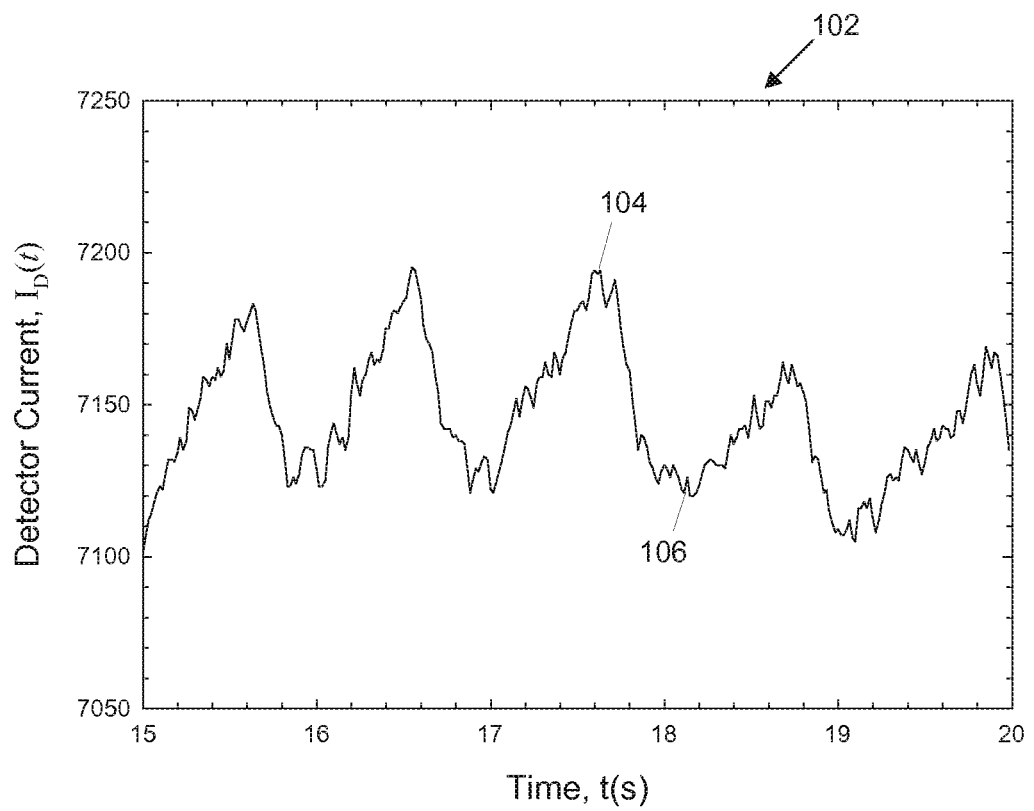
FIG. 1 illustrates a plot of a pulse wave corresponding to light absorption of arterial blood, according to exemplary embodiments.

FIG. 1 depicts a plot 102 of a detector photocurrent, $I_D(t)$, that corresponds to the power of light received by a detector after the light has passed through a subject's finger. As can be seen, the detector photocurrent exhibits a cyclic pattern. This cyclic pattern is due to the subject's heartbeat, which cyclically increases and decreases the quantity of blood in the subject's capillaries (or other structures). Although the magnitude of the cyclic pattern is small in comparison to the total photocurrent generated by the detector, considerable information can be extracted from the cyclic pattern of the plot 102. For example, assuming that the person's heart rate is sixty beats per minute, the time between the start of any pulse beat and the end of that pulse beat is one second. During this one-second period, the photocurrent will have a maximum or peak reading 104 and minimum or valley reading 106. The peak reading 104 of the plot corresponds to when there is a minimum amount of blood in the capillaries, and the valley reading 106 corresponds to when there is a maximum amount of blood in the capillaries. By using information provided by the peak and valley of the cyclic plot, the optical absorption and scattering by major finger constituents that are not in the capillaries, such as skin, fat, bones, muscle and interstitial fluids, are excluded. These major constituents that are not in the capillaries are excluded because they are not likely to change during the time interval of one heartbeat. In other words, the light that is absorbed and scattered, attenuated, by the blood can be detected based on the peaks and valleys of the plot 102.

Assuming that the peak of the cyclic photocurrent generated by the light-sensing device is $I_p$, the adjacent valley of the cyclic photocurrent is $I_v$, and the photocurrent generated by the light-sensing device without a human finger is $I_0$, the transmittances corresponding to the peak and valley photocurrents can be defined as:

$$T_V = \frac{I_V}{I_0} \qquad (1)$$

and $$T_P = \frac{I_P}{I_0} \qquad (2)$$

The corresponding peak and valley absorbance are:

$$A_v = -\log(T_v) \qquad (3)$$

and $$A_p = -\log(T_p) \qquad (4)$$

The difference between $A_v$ and $A_p$ represents the light absorption and scattering by the blood in the finger, excluding non-blood constituents:

$$\Delta A = A_V - A_P = \log\left(\frac{I_P}{I_V}\right) \qquad (5)$$

As can be seen in the algorithm shown in Equation (5), $\Delta A$ does not depend on $I_0$. Thus, calculating $\Delta A$ does not require a determination of the current generated by the light-sensing device without a sample. Monitoring the photocurrent corresponding to light power transmitted through a sample is sufficient to calculate $\Delta A$.

Figure 2:
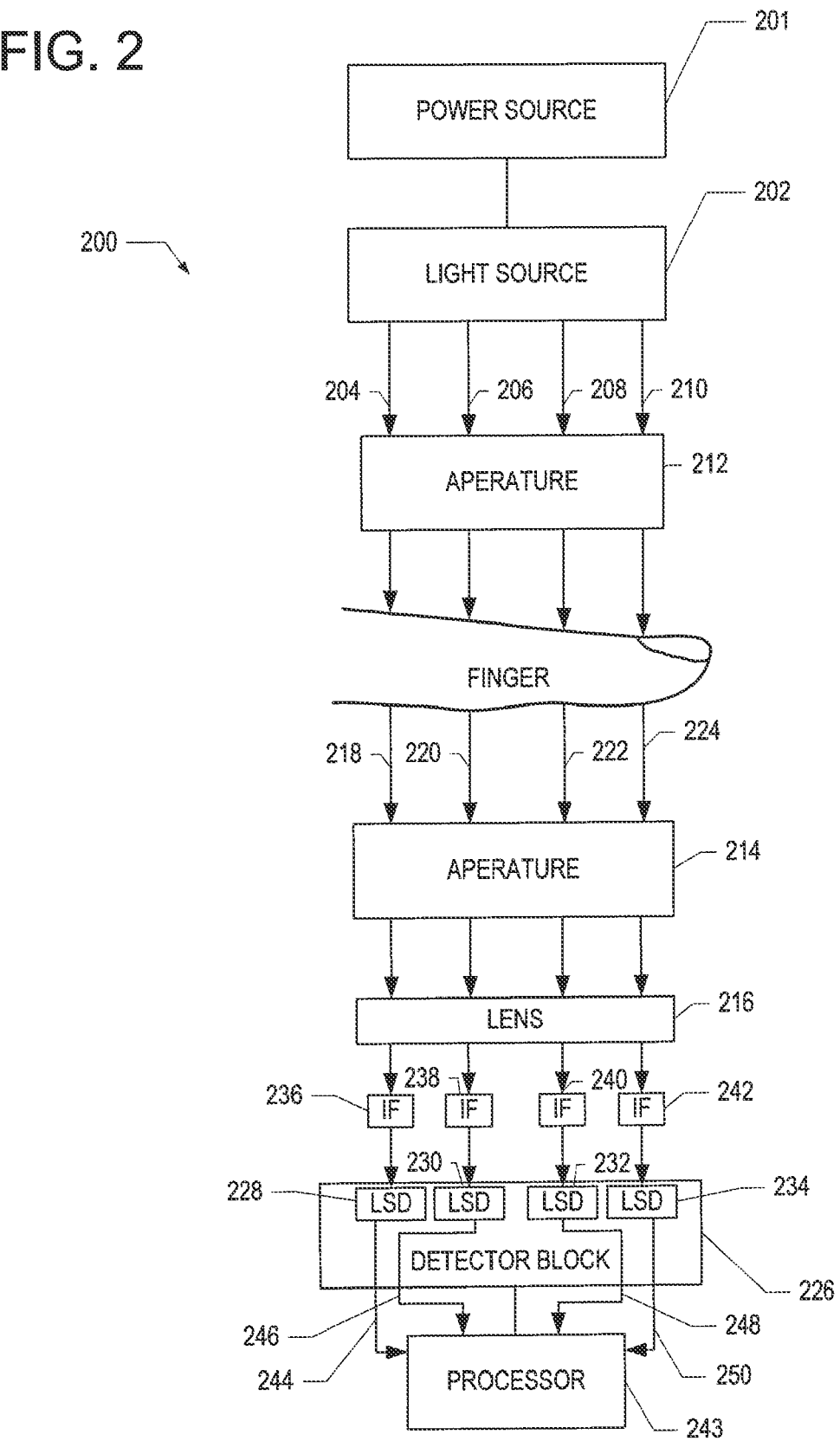
FIG. 2 illustrates an exemplary system for obtaining spectral data.

FIG. 2 depicts a simplified block diagram of an exemplary apparatus for use in an exemplary embodiment. Optical measurement system, which is generally indicated by numeral 200, uses the "pulsatile" concept for determining an amount of light absorbed and scattered solely by the blood in a sample (a human finger in this exemplary embodiment). A power source 201, such as a battery, provides power to a light source 202 that generates a plurality of light beams 204, 206, 208, 210 that are directed toward the top of the finger of a subject. In an exemplary embodiment, each of the light beams 204, 206, 208, 210 have the same wavelength or a different wavelength range, typically within 800 nm to 1600 nm. Although the optical measurement system 200 is described herein as generating four (4) light beams, it is contemplated that the light source 202 can be altered to generate fewer light beams or additional light beams in other embodiments.

A first aperture 212 ensures that the light beams 204, 206, 208, 210 strike a target area of the finger. A second aperture 214 ensures that the portion of the light beams that are transmitted through the finger strike a lens 216. Light beams 204, 206, 208, 210 are attenuated by the finger and components of the optical measurement system 200, and, thus, attenuated light beams 218, 220, 222, 224 are emitted from the finger. The attenuated light beams 218, 220, 222, 224 strike the lens 216, and the lens 216 collects the attenuated light beams 218, 220, 222, 224 so that they impinge more efficiently on a detector block 226.

The detector block 226 is positioned directly under the lens 216 and comprises a plurality of light-sensing devices (LSD) 228, 230, 232, 234 such as an array of photodiodes. According to one aspect of the optical measurement system 200, each of the light-sensing devices 228, 230, 232, 234 detects a specific wavelength of light as defined by corresponding interference filters (IF) 236, 238, 240, 242, respectively. The interference filter transmits one or more spectral bands or lines of light, and blocks others.

Each of the light-sensing devices 228, 230, 232, 234 generates a corresponding photocurrent signal that is proportional to the power of the light received by the particular light sensing device. The photocurrent signal generated by the photodiode can be converted to another form of signal, such as an analog voltage signal or a digital signal. A processor 243 is coupled to the detector block 226 and is configured to calculate the change of photocurrent signals 244, 246, 248, 250.

According to one aspect, the processor 243 executes an algorithm such as shown in the Equation (5) to calculate the change in the light absorption ($\Delta A$) solely caused by the blood in the finger. Thereafter, this quantitative calculation of light absorption of the blood can be used to determine a characteristic of the blood. For example, by comparing the calculated light absorption value to predetermined values corresponding to different glucose levels stored in a memory (not shown), a blood-glucose level of the subject can be determined.

A difficulty associated with the finger based pulsatile detection methodology is low signal-to-noise (S/N) ratio, because the amplitude of cyclic pattern (i.e., the difference between peak and valley) is typically 1%-2% of the total photocurrent generated by the light power transmitted through the finger. To obtain a S/N ratio of 100:1 in the determination of $\Delta A$, the baseline noise of the device being used to measure the light absorption by the finger should not be larger than $3.0 \times 10^{-5}$ in absorbance (peak to peak), within a 10 Hz bandwidth.

However, a $3.0 \times 10^{-5}$ absorbance (peak to peak) baseline noise level within a 10 Hz bandwidth is difficult to obtain with the low light power levels that are used by some battery-powered hand held non-invasive blood chemical measurement devices. One solution involves data averaging. To increase the S/N ratio, the averaged value of $\Delta A$, as defined by the Equation below, is used in further calculation to extract blood glucose concentration:

$$\overline{\Delta A} = \sum_{j=1}^{M} \Delta A_j \qquad (6)$$

In Equation (6), M is the number of heartbeats during the time interval of the pulsatile measurement. However, this approach requires long data acquisition time, due to the fact that the rate of heartbeat is in the order of one per second. For example, 25 seconds would be needed fir increasing the S/N ratio by a factor of five, and 100 seconds would be needed for increasing the S/N ratio by a factor often. In comparison, current commercial blood drawing glucose meters can determine blood glucose level within 5 seconds. Furthermore, long detection time will significantly increase measurement errors due to finger movement, light power drift, device temperature change, etc. Thus, there is a need for new techniques to measure blood glucose levels quickly and accurately.

Improving S/N Ratio by Standard Deviation

The time dependent detector photocurrent output, $I_D(t)$, shown in FIG. 1 can be expressed as the sum of a small time dependent cyclic photocurrent $\Delta I(t)$, corresponding to the heartbeat, a noise current $n(t)$, and a constant baseline photocurrent $I_B$:

$$I_D(t) = I_B + \Delta I(t) + n(t) \qquad (7)$$

The above Equation can be re-arranged as:

$$\frac{I_D(t)}{I_B} = 1 + \frac{\Delta I(t) + n(t)}{I_B} \qquad (8)$$

Applying common logarithm to both side of the Equation (8), one obtains:

$$A(t) = \log\left[\frac{I_D(t)}{I_B}\right] = \log\left(1 + \frac{\Delta I(t) + n(t)}{I_B}\right) \qquad (9)$$

Figure 3:
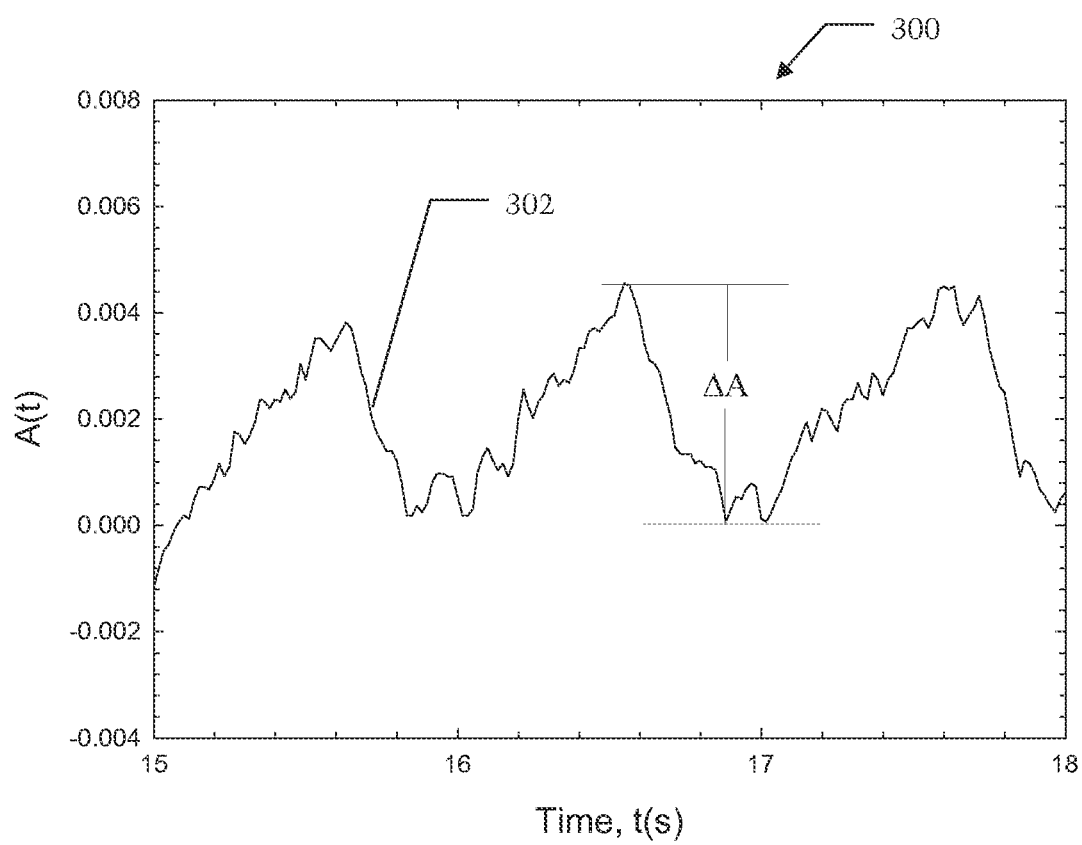
FIG. 3 illustrates a plot of A(t), calculated according to Equation (9) using data in FIG. 1.

FIG. 3, which is generally indicated by numeral 300, shows a typical A(t) plot 302, calculated according to Equation (9) using data in FIG. 1. For a pulse function A(t) shown in FIG. 3, the following key relationship exists during the time interval of one heartbeat:

$$\sigma[A(t)] = k\Delta A \qquad (10)$$

in which $\sigma[A(t)]$ is the Standard Deviation of A(I), and k is a proportional constant.

Considering the fact that $I_B$ is a constant and $\sigma^2(\log I_B) = 0$, one obtains:

$$\sigma[A(t)] = \sigma[\log I_D(t)] \qquad (12)$$

Therefore, the peak-to-valley height of the A(t) plot during the time interval of one heartbeat can be obtained directly from the standard deviation of the logarithm of $I_D(t)$:

$$\Delta A = \frac{\sigma[A(t)]}{k} = \frac{\sigma[\log I_D(t)]}{k} \qquad (13)$$

A major advantage of Equation (13) is that high S/N ratio can be achieved within short data acquisition time (approximately one second), as explained below.

In a finger based pulsatile measurement depicted by FIG. 2, the value of the sum, $\Delta I(t)+n(t)$ is typically less than 2% of the large constant baseline photocurrent $I_B$. Therefore, Equation (9) can be approximated as:

$$A(t) = \log\left[\frac{I_D(t)}{I_B}\right] \approx \frac{1}{\ln 10} \frac{\Delta I(t) + n(t)}{I_B} \tag{14}$$

Similarly, the standard deviation of A(t) can be approximated as:

$$\sigma[A(t)] \approx \frac{1}{\ln 10} \frac{\sqrt{\sigma^2[\Delta I(t)] + \sigma^2[n(t)]}}{I_B} \tag{15}$$

Equation (15) demonstrates great noise reduction power of Equation (13). For example, for a relatively high baseline noise with the ratio $$\rho = \frac{\sigma[n(t)]}{\sigma[\log \Delta I(t)]} = 0.1 (\text{or } 10\%),$$

the contribution to $\sigma[A(t)]$ from the baseline noise n(t) is estimated to be less than 0.005 (or 0.5%), corresponding to an increase in S/N ratio by a factor of 20 without increasing detection time. As such, dramatic noise reduction can be obtained without increasing the data acquisition time, and a finger based pulsatile measurement can be completed within the time interval of one heartbeat (which is approximately one second), and the requirement for the S/N ratio of 100 to 1 in determination of $\Delta A$ can be satisfied using an optical system with a baseline noise of about $6.0\times10^{-4}$ absorbance (peak to peak) within a 10 bandwidth. It should be pointed out that when the baseline noise of an optical system is dominated by shot noise due to low light illumination power, a noise reduction by a factor of 20 equals an increasing in light illumination power by a factor of 20 2=400.

This ability of obtaining higher S/N ratio within the very short data acquisition time, e.g., less than one second, will significantly reduce detection error caused by factors such as finger movement, temperature change, and light power drift during the measurement, and therefore dramatically improve the accuracy and reproducibility of the pulsatile detection methodology.

Furthermore, the value of k does not change with wavelength, because transmitted lights at all wavelengths have identical pulse shape due to the heartbeat. As a result, the constant k will be cancelled in data normalization discussed in next section, and $\sigma[\log I_D(t)]$ will be used in further regression analysis to establish correlation between the optical measurement and blood glucose level. This will greatly simplify the data analysis process since $\sigma[\log I_D(t)]$ involves only two standard math functions available in most popular spreadsheet programs such as Microsoft EXCEL®, EXCEL® is a federally registered trademark of Microsoft Corporation, having a place of business at One Microsoft Way, Redmond, Washington 98052-6399.

Normalization

At each wavelength $\lambda_i$, the absorption $\Delta A(\lambda_i)$ is linked to the increase of amount of blood ($\Delta B$) in the optical sensing area of the fingertip due to the heartbeat by the following Equation:

$$\Delta A(\lambda_i) = \varepsilon(C, \lambda_i, T)\Delta B \tag{16}$$

in which $\varepsilon(C, \lambda_i, T)$ is the absorption/scattering coefficient of blood at wavelength finger temperature T, and blood glucose concentration C. It is well understood that the variable $\Delta B$ differs from person to person, and may even change from day to day for the same person.

The uncertainty from the variable $\Delta B$ can be cancelled by introducing the normalization factor $Q_i(C,T)$ at each wavelength $\lambda_i$, as defined by the Equation below:

$$Q_i(C, T) = \frac{\Delta A(\lambda_i)}{\sum_{i=1}^{N}\Delta A(\lambda_i)} = \frac{\varepsilon(C, \lambda_i, T)}{\sum_{i=1}^{N}\varepsilon(C, \lambda_i, T)}, \tag{17}$$

in which N is total number of wavelength employed. Preferably, N typically ranges from twenty to thirty.

Based on Equations (13) and (17), $Q_i(C,T)$ is linked to the detector photocurrent at each wavelength $\lambda_i$, $I_D(\lambda_i,T)$ by the following Equation:

$$Q_i(C, T) = \frac{\Delta A(\lambda_i)}{\sum_{i=1}^{N}\Delta A(\lambda_i)} = \frac{\sigma[\log I_D(\lambda_i, t)]/k}{\sum_{i=1}^{N}\sigma[\log I_D(\lambda_i, t)]/k} = \frac{\sigma[\log I_D(\lambda_i, t)]}{\sum_{i=1}^{N}\sigma[\log I_D(\lambda_i, t)]}, \tag{18}$$

As shown by Equation (18), the constant k is cancelled and $\sigma[\log I_D(t)]$ will be used in further regression analysis to establish correlation between the optical measurement and blood glucose level. This is possible because data are taken simultaneously from all detection channels.

A correlation between optical measurement and blood glucose concentration can be established according to the following Equation:

$$C_{optical} = \sum_{i=1}^{N} a_i(T)Q_i(C, T) \tag{19}$$

in which $C_{optical}$ is the blood glucose concentration predicted by the optical measurement, $Q_i(C,T)$ is defined by Equations (17) and (18), and $a_i(T)$ is the temperature dependent regression coefficient corresponding to wavelength $\lambda_i$. The values of $a_i(T)$ can be extracted using proper statistics methods such as Partial Least Squares (PLS) regression.

Equation (19) represents ideal cases when large number of calibrations can be made at different finger temperatures. In reality, frequently only a limited number of calibrations can be made (e.g., 15 to 20), and each may be taken at a different finger temperature. Under this condition, the finger temperature can be treated as an independent variable, and the above Equation can be approximated as:

$$C_{optical} = \sum_{i=1}^{N} b_i Q_i(C, T) + \eta T \tag{20}$$

in which $b_i$ is the temperature independent regression coefficient corresponding to wavelength $\lambda_i$, and $\eta$ is the regression coefficient for the finger temperature. The values of $b_i$ and that of $\eta$ can be extracted using proper statistics methods such as Partial Least Squares (PLS) regression.

Ratio Methodology

Alternatively, the uncertainty from the variable $\Delta B$ can be cancelled by introducing a ratio factor $Y_{ij}$ at wavelength $$Y_{ij}(C, T) = \frac{\Delta A(\lambda_i)}{\Delta A(\lambda_j)} = \frac{\varepsilon(C, \lambda_i, T)}{\varepsilon(C, \lambda_j, T)} = \frac{\sigma[\log I_D(\lambda_i, t)]}{\sigma[\log I_D(\lambda_j, t)]}, \quad (21)$$

in which j can be any number from 1 to N, assuming that the device collects signal at all N wavelengths.

Similar to the normalization algorithm discussed before, a correlation between optical measurement and blood glucose level can be established according to the following Equation:

$$C_{optical} = \sum_{i \neq j}^{N} f_i(T) Y_{ij}(C, T) \quad (22)$$

in which $C_{optical}$ is the blood glucose concentration predicted by the optical measurement, $Y_{ij}(C,T)$ is defined by Equation (21), and $f_i(T)$ is the temperature dependent regression coefficient corresponding to wavelength $\lambda_i$. The value of $f_i(T)$ can be obtained using statistics methods such as Partial Least Squares (PLS) regression.

Equation (22) represents ideal cases when large number of calibration can be made at different finger temperatures. In reality, frequently only limited number of calibration can be made (e.g., 15 to 20), and each may be taken at a different finger temperature. Under this condition, the finger temperature can be treated as an independent variable, and the above Equation can be approximated as:

$$C_{optical} = \sum_{i \neq j}^{N} h_i Y_{ij}(C, T) + \beta T \quad (23)$$

in which $h_1$ is the temperature independent regression coefficient corresponding to wavelength $\lambda_i$, and $\beta$ is the regression coefficient for the finger temperature. The values of $h_1$ and that of $\beta$ can be extracted using proper statistics methods such as Partial Least Squares (PLS) regression.

Elimination of the Effect of Temperature Dependent Device Response

It is well understood that the detector sensitivity of a silicon photodiode detector is a function of wavelength and temperature. For the device configuration shown in FIG. 2, which is generally indicated by numeral 200, the light power received by ith silicon diode detector, corresponding to wavelength $\lambda_i$, is converted into a photocurrent according to the following Equation:

$$I_D(\lambda_i, t) = P(\lambda_i, t) S_0(\lambda_i)[1 + \gamma(\lambda_i)(T_{Di}, t) - 25° C.)] \quad (24)$$

In the above Equation (24), $P(\lambda_i, t)$ is the light power received by the detector, $S_0(\lambda_i)$ is the photosensitivity of the detector at wavelength $\lambda_i$ and 25° C., $\gamma(\lambda_i)$ is the temperature coefficient of the photosensitivity at wavelength $\lambda_i$, and $T_{Di}(t)$ is the temperature of ith photodiode detector. The temperature coefficient $\gamma(\lambda_i)$ varies with the wavelength. For example, for Hamamatsu S1337 series photodiode detectors, $\gamma(\lambda_i)$ ranges from near zero at 900 nm to over 1.0%/° C. at 1100 nm. This imposes a potential problem for the device configuration show in FIG. 2, because it is very difficult to keep temperature of each individual diode detector constant in a handheld device used by a person with diabetes under a normal household/office environment. This uncertainty due to the detector temperature T (I) can be eliminated using the algorithm shown by Equations (12) and (13). Applying common logarithm on both sides of the Equation (24), one obtains:

$$\log I_D(\lambda_i, t) = \log P(\lambda_i, t) + \log S_0(\lambda_i) + \log [1 + \gamma(\lambda_i)(T_{Di}(t) - 25° C.)] \quad (25)$$

Considering the fact that $S_0(\lambda_i)$ is a constant and that detector temperature $T_{Di}(t)$ remains almost constant during the very short data acquisition time interval of approximately one second, one obtains:

$$\sigma[\log I_D(\lambda_i, t)] = \sigma[\log P(\lambda_i, t)] \quad (26)$$

As such, the uncertainty caused by detector temperature $T_{Di}(t)$ is eliminated by the use of this standard deviation methodology.

Voltage Detection Mode

Figure 4:
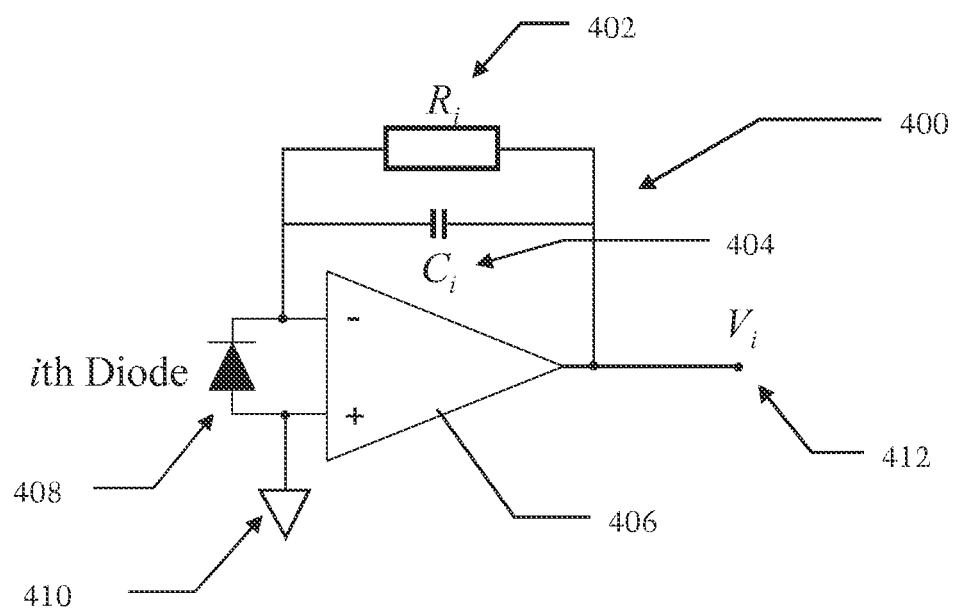
FIG. 4 is a basic illustrative schematic of a preamplifier circuit that converts photocurrent into voltage prior to digitization.

In the device configuration shown in FIG. 2, the photocurrent of ith photodiode detector $I_D(\lambda_i, t)$ is typically converted into a voltage using a preamplifier before digitization. FIG. 4 shows the schematic circuit diagram of a typical preamplifier, which is generally indicated by numeral 400.

The output voltage 412 of ith preamplifier 400, in coupling with ith photodiode detector 408, can be expressed as:

$$V_i(t) = R_i I_D(\lambda_i, t) = R_{0i}[1 \pm \chi_i(T_{Ri}(t) - 25° C.)] I_D(\lambda_i, t) \quad (27)$$

In the above Equation (27), R oi is the resistance value of feedback resistor 402 tier ith preamplifier at 25° C., $\chi_i$ is the temperature coefficient of the resistor, and $T_{Ri}(t)$ is the temperature of the resistor. Applying common logarithm to both side of the Equation (27), one obtains:

$$\log V_i(t) = \log R_{i0} + \log[1 + \chi_i(T_{Ri}(t) - 25° C.)] + \log I_D(\lambda_i, t) \quad (28)$$

Considering the fact that R oi is a constant and that the resistor temperature $T_{Ri}(t)$ does not change during the very short data acquisition time interval of approximately one second, one obtains:

$$\sigma[\log V_i(t)] = \sigma[\log I_D(\lambda_i, t)] \quad (29)$$

Substituting Equation (26) into Equation (29), one obtains:

$$\sigma[\log V_i(t)] = \sigma[\log P(\lambda_i, t)] \quad (30)$$

As such, the uncertainty caused by resistor temperature $T_R(t)$ is eliminated.

Under the voltage detection mode, the normalization factor in Equation (18) can be expressed as:

$$Q_i(C, T) = \frac{\sigma[\log V_i(t)]}{\sum_{i=1}^{N} \sigma[\log V_i(t)]} \quad (31)$$

The mathematic correlation between optical measurement and blood glucose concentration can then be established according to Equation (19) or Equation (20), under corresponding calibration conditions.

Similarly, the ratio factor defined by Equation (21) can be expressed as:

$$Y_{ij}(C, T) = \frac{\sigma[\log V_i(t)]}{\sigma[\log V_j(t)]} \quad (32)$$

The mathematic correlation between optical measurement and blood glucose concentration can then be established according to Equation (22) or Equation (23), under corresponding calibration conditions. The schematic circuit diagram of a typical preamplifier 400 also includes a feedback capacitor 404, an operational amplifier 406, and a ground connection 410.

Digitization

The voltage output 412 from the preamplifier 400 is usually digitized using an analog-to-digital convertor (ADC). The digitized signal is then sent to a computer fir data analysis. The output of ith ADC, in communication with ith preamplifier that is in coupling with ith photodiode 408 collecting light power at wavelength $\lambda_i$, can be expressed by the following Equation:

$$(ADC)_i = (ADC)_{0i} + G_i\{[I_D(\lambda_i,t) + I_{Dark,i}]R_i + A_{0i}\} \qquad (33)$$

In the above Equation (33), $(ADC)_{0i}$ is the offset of ith ADC, $G_i$ is the nominal ADC Gain used during the detection, $I_D(\lambda_i,t)$ is the photocurrent of ith photodiode detector, $I_{Dark,i}$ is the dark current of ith photodiode detector, $R_i = R_{0i}[1+\chi_i(T_{Ri}(t)-25°\text{ C.})]$ is the resistance of feedback resistor of ith preamplifier, and $A_{0i}$ is the offset of ith preamplifier.

The contribution of the three factors, $(ADC)_{0i}$, $I_{Dark,i}$, and $A_{0i}$ can be removed by carrying out a dark measurement with the light source turned off right before or after the corresponding finger measurement. When the light source is turned off, the above Equation (33) becomes:

$$(ADC)_{Dark,i} = (ADC)_{0i} + G_i(I_{Dark,i}R_i + A_{0i}) \qquad (34)$$

The difference between the two above Equations (33) and (34) reflects ADC output corresponding to the photocurrent:

$$\Delta(ADC)_i = (ADC)_i - (ADC)_{Dark,i} = G_i I_D(\lambda_i,t) \qquad (35)$$

Applying common logarithm to both side of the Equation (35), one obtains:

$$\log \Delta(ADC)_i = \log G_i + \log I_D(\lambda_i,t) + \log R_i \qquad (36)$$

$G_i$ and $R_i$ can be considered as constants as long as the thine interval between the finger measurement and the dark measurement is short. As such, one obtains:

$$\sigma[\log \Delta(ADC)_i] = \sigma[\log I_D(\lambda_i,t)] \qquad (37)$$

Substituting Equation (26) into Equation (37), one further obtains:

$$\sigma[\log \Delta(ADC)_i] = \sigma[\log P(\lambda_i,t)] \qquad (38)$$

Based on Equation (37), the normalization factor defined by Equation (18) can be expressed as:

$$Q_i(C,T) = \frac{\sigma[\log \Delta(ADC)_i]}{\sum_{i=1}^{N}\sigma[\log \Delta(ADC)_i]} \qquad (39)$$

The mathematic correlation between optical measurement and blood glucose concentration can then be established according to Equation (19) or (20), under corresponding calibration conditions.

Similar to normalization, the ratio factor defined by Equation (21) can be expressed as:

$$Y_{ij}(C,T) = \frac{\sigma[\log \Delta(ADC)_i]}{\sigma[\log \Delta(ADC)_j]} \qquad (40)$$

The correlation between optical measurement and blood glucose concentration can then be established according to Equations (22) or (23), under corresponding calibration conditions.

Thus, there has been shown and described several embodiments of a novel invention. As is evident from the foregoing description, certain aspects of the present invention are not limited by the particular details of the examples illustrated herein, and it is therefore contemplated that other modifications and applications, or equivalents thereof, will occur to those skilled in the art. The terms "have," "having," "includes," "including," and similar terms as used in the foregoing specification are used in the sense of "optional" or "may include" and not as "required." Many changes, modifications, variations and other uses and applications of the present construction will, however, become apparent to those skilled in the art after considering the specification and the accompanying drawings. All such changes, modifications, variations and other uses and applications, which do not depart from the spirit and scope of the invention, are deemed to be covered by the invention, which is limited only by the claims that follow. It should be understood that the embodiments disclosed herein include any and all combinations of features described in any of the dependent claims.

The invention claimed is:

1. A system for detecting glucose in a biological sample, comprising:

at least one light source configured to generate one or more light beams to strike a target area of a sample;

at least one light detector positioned to receive light from the at least one light source and to generate an output signal, comprising a time dependent current, which is indicative of a power of light detected;

a light absorbance change determining algorithm implemented processor programmed to calculate a change in a light absorption caused by blood in the biological sample and configured to receive the output signal from the at least one light detector and based on the received output signal, calculate the attenuance attributable to blood in a sample present in the target area with either a normalization factor or a ratio factor, eliminate effect of uncertainty caused by temperature dependent detector response of the at least one light detector, and based on the calculated attenuance, determine a blood glucose level associated with a sample present in the target area;

an analog-to-digital converter comprising a digitized voltage output, wherein the light absorbance change determining algorithm implemented processor is configured to calculate the normalization factor $Q_i(C,T)$ based on an analog-to-digital converter voltage output $\Delta(ADC)_i$ of an $i^{th}$ analog-to-digital converter, where $\sigma$ is a standard deviation according to an equation:

$$Q_i(C,T) = \frac{\sigma[\log\Delta(ADC)_i]}{\sum_{i=1}^{N}\sigma[\log\Delta(ADC)_i]}$$

or a ratio factor $Y_{ij}(C,T)$ based on the analog-to-digital converter voltage output $\Delta(ADC)_i$ of the $i^{th}$ analog-to-digital converter and an analog-to-digital converter voltage output $\Delta(ADC)_j$ of a $j^{th}$ analog-to-digital converter, where $\sigma$ is a standard deviation according to the equation:

$$Y_{ij}(C, T) = \frac{\sigma[\log\Delta(ADC)_i]}{\sigma[\log\Delta(ADC)_j]},$$

wherein T is a temperature of the biological sample and C is a concentration of blood glucose in the biological sample.

2. The system for detecting glucose in a biological sample according to claim 1, wherein the light absorbance change determining algorithm implemented processor is configured to eliminate the effect of uncertainty caused by temperature dependent detector response of the at least one light detector by calculating a standard deviation of the logarithm of the time dependent output current generated by the light power from the same target area of the biological sample.

3. The system for detecting glucose in a biological sample according to claim 1, wherein the at least one light detector includes a preamplifier comprising a feedback resistor.

4. A system for detecting glucose in a biological sample comprising:
- at least one light source configured to generate one or more light beams to strike a target area of a sample;
- at least one light detector positioned to receive light from the at least one light source and to generate an output signal, comprising a time dependent current, which is indicative of avower of light detected;
- a light absorbance change determining algorithm implemented processor programmed to calculate a change in a light absorption caused by blood in the biological sample and configured to receive the output signal from the at least one light detector and based on the received output signal, calculate the attenuance attributable to blood in a sample present in the target area with either a normalization factor or a ratio factor, eliminate effect of uncertainty caused by temperature dependent detector response of the at least one light detector, and based on the calculated attenuance, determine a blood glucose level associated with a sample present in the target area; and
- an analog-to-digital convertor comprising a digitized voltage output, wherein the light absorbance change determining algorithm implemented processor is configured to calculate the normalization factor $Q_i(C,T)$ based on the analog-to-digital convertor voltage output $\Delta(ADC)$, of the $i^{th}$ analog-to-digital converter, where $\sigma$ is standard deviation according to an equation:

$$Q_i(C, T) = \frac{\sigma[\log\Delta(ADC)_i]}{\sum_{i=1}^{N} \sigma[\log(ADC)_i]}$$

or a ratio factor $Y_{ij}(C,T)$ based on the analog-to-digital convertor voltage output $\Delta(ADC)_i$ of the $i^{th}$ analog-to-digital convertor and the analog-to-digital convertor voltage output $\Delta(ADC)$, of the $j^{th}$ analog-to-digital convertor, where $\sigma$ is standard deviation according to an equation:

$$Y_{ij}(C, T) = \frac{\sigma[\log\Delta(ADC)_i]}{\sigma[\log\Delta(ADC)_j]},$$

wherein T is the temperature of the biological sample and C is the concentration of blood glucose in the biological sample.

5. A system for detecting glucose in a biological sample comprising:
- at least one light source configured to generate one or more light beams to strike a target area of a sample;
- at least one light detector positioned to receive light from the at least one light source and to generate an output signal, comprising a time dependent current, which is indicative of a power of light detected;
- a light absorbance change determining algorithm implemented processor programmed to calculate a change in a light absorption caused by blood in the biological sample and configured to receive the output signal from the at least one light detector and based on the received output signal, calculate the attenuance attributable to blood in a sample present in the target area, eliminate effect of uncertainty caused by temperature dependent detector response of the at least one light detector, and based on the calculated attenuance, determine a blood glucose level associated with a sample present in the target area; and
- an analog-to-digital convertor comprising a digitized voltage output, wherein the light absorbance change determining algorithm implemented processor is configured to eliminate the effect of uncertainty caused by temperature dependent detector response of the at least one light detector by calculating a standard deviation of the logarithm of the time dependent output current generated by the light power from the same target area of the biological sample, wherein the light absorbance change determining algorithm implemented processor is configured to calculate a normalization factor $Q_i(C,T)$ based on the analog-to-digital convertor voltage output $\Delta(ADC)$, of the $i^{th}$ analog-to-digital converter, where $\sigma$ is standard deviation according to an equation:

$$Q_i(C, T) = \frac{\sigma[\log\Delta(ADC)_i]}{\sum_{i=1}^{N} \sigma[\log\Delta(ADC)_i]}$$

or a ratio factor $Y_{ij}(C,T)$ based on the analog-to-digital convertor voltage output $\Delta(ADC)_i$ of the $i^{th}$ analog-to-digital convertor and the analog-to-digital convertor voltage output $\Delta(ADC)_j$ of the $j^{th}$ analog-to-digital convertor, where $\sigma$ is standard deviation according to the equation:

$$Y_{ij}(C, T) = \frac{\sigma[\log\Delta(ADC)_i]}{\sigma[\log\Delta(ADC)_j]},$$

wherein T is the temperature of the biological sample and C is the concentration of blood glucose in the biological sample.

6. The system for detecting glucose in a biological sample according to claim 5, wherein the at least one light detector includes a preamplifier comprising a feedback resistor.

* * * * *